United States Patent [19]

Ibrahim et al.

[11] Patent Number: 6,057,135
[45] Date of Patent: May 2, 2000

[54] PROCESS FOR MANUFACTURING D-TAGATOSE

[75] Inventors: Osama O. Ibrahim, Stockholm, N.J.; Joseph E. Spradlin, Monroe, N.Y.

[73] Assignee: Kraft Foods, Inc., Northfield, Ill.

[21] Appl. No.: 07/976,241

[22] Filed: Nov. 13, 1992

Related U.S. Application Data

[63] Continuation-in-part of application No. 07/821,969, Jan. 16, 1992, abandoned.

[51] Int. Cl.[7] .............................. C12P 19/02; C07H 1/00; C07G 17/00
[52] U.S. Cl. ........................ 435/105; 536/1.11; 536/124; 536/127; 426/658
[58] Field of Search ............................ 435/105; 536/125, 536/53, 29.12, 127, 124, 1.11; 426/658; 127/46.1

[56] References Cited

U.S. PATENT DOCUMENTS

| | | | |
|---|---|---|---|
| 4,069,104 | 1/1978 | Barker et al. | 536/1.1 |
| 4,595,659 | 6/1986 | Roland et al. | 435/135 |
| 4,786,722 | 11/1988 | Zehner | 536/125 |
| 4,976,975 | 12/1990 | Callanain | 426/36 |
| 5,002,612 | 3/1991 | Beadle et al. | 536/125 |

FOREIGN PATENT DOCUMENTS

| | | |
|---|---|---|
| 60248196 | of 0000 | Japan. |
| 1497888 | 1/1978 | United Kingdom. |

OTHER PUBLICATIONS

Fiehring, et al; Chem Abstract, vol. 73(25) p129742e (1970).

Hartley et l, Chem Abstract, vol. 114(25) p242021x (1990).

K. Yamanaka et al., "L–Arabinose Isomerase", Methods in Enzymology, Carbohydrate Metabolism, (edited by Willis A. Wood, 1996), pp. 596–602, vol. IX.

T. Nakamatu et al., "Crystallization and properties of L–arabinose Isomerase from *Lactobacillus Gayonii*", Kagawa University, BBA 65867, *Biochim, Biophys, Acta*, 178 (1969) pp. 156–165.

F.J. Simpson et al., "Degradation of L–Arabinose by Aerobacter Aerogenes", The Journal of Biological Chemistry, vol. 230 (1958) pp. 457–472.

K. Izumori et al. "Pentose Metabolism in *Mycobacterium smegmatis*: Comparison of L–Arabinose Isomerases induced by L–Arabinose and D–Galactose" *Journal of Bacteriology*, Jan. 1978, pp. 412–414, vol. 133 No. 1.

J.R. Ernandes et al., "Simultaneous Utilization of Galactose and Glucose by Saccharomyces spp.", Biotechnology Technique, vol. 6, No. 3, May/Jun. 1992, pp. 233–238.

P.J. Whalen, "Development, Scale–up and a Continuous Fermentation Process for the Cofermentation of Cheese Whey and Corn for Ethanol Production", University of Nebraska, Lincoln, NE 68583–0745 U.S.A., Dissertation Abstracts International, B1988, 49(4) 964–965.

T. Miyamoto et al., Japanese Journal of Dairy and Food Science, 1986, 35(4) A143–150.

V.S. O'Leary et al., "Influence of Lactose Hydrolysis and Solids Concentration on Alcohol Production by Yeast in Acid Whey Ultrafiltrate", Biotechnology and Bioengineering, vol. XIX, (1977) pp. 1689–1702.

(List continued on next page.)

*Primary Examiner*—Louise N. Leary
*Attorney, Agent, or Firm*—Thomas A. Marcoux; Thomas R. Savoie

[57] ABSTRACT

D-tagatose is manufactured from cheese whey and/or milk. The cheese whey and/or milk is hydrolyzed to prepare a mixture comprising galactose and glucose. Galactose is separated from the glucose by fermentation and subjected to isomerization using L-arabinose isomerase, thereby producing D-tagatose. The D-tagatose can be used as a reduced calorie food sweetening and bulking agent, as an intermediate for the synthesis of optically active compounds, and as an additive in detergent, cosmetic and pharmaceutical formulations.

8 Claims, 1 Drawing Sheet

OTHER PUBLICATIONS

D.W. Koren et al., "Continuous Production of Fructose Syrup and Ethanol from Hydrolysed Jerusalem Artichoke Juice", Journal of Industrial Microbiology, 7 (1991) pp. 131–136.

Z. Duvnjak et al., "Production of Sorbitol and Ethanol from Jerusalem Artichokes by *Saccharomyces cerevisiae* ATCC 36859", Applied Microbiology Biotechnology (1991) 35:711–715.

J.W. Patrick et al., "Coordination of Enzyme Synthesis in the L–Arabinose Operon in *Escherichia col*", J. Biol Chem, 1071, 246, 5102–6.

PROCESS FOR MANUFACTURING D-TAGATOSE

CROSS-REFERENCE TO RELATED APPLICATION

This application is a continuation-in-part of application Ser. No. 07/821,969, filed Jan. 16, 1992, abandoned.

BACKGROUND OF THE INVENTION

1. Field of the Invention

The present invention has to do with a method of manufacturing D-tagatose from cheese whey and/or milk. More particularly, the invention relates to a method of producing D-tagatose by employing L-arabinose isomerase in the enzymatic isomerization of D-galactose recovered from the fermentation of a lactose hydrolysate. The lactose hydrolysate is derived from cheese whey and/or milk. D-tagatose is useful as a low calorie sweetener or bulking agent.

2. Description of Related Art

D-tagatose is the keto sugar of D-galactose. It has a sweetness equivalent to fructose but is poorly digested. Thus it can be used as a reduced calorie food sweetening and bulking agent. D-tagatose is also useful as an intermediate for the synthesis of other optically active compounds and as an additive in detergent, cosmetic and pharmaceutical formulations. D-tagatose is non-cariogenic and reduces insulin demand.

D-tagatose is presently made from D-galactose by chemical synthesis. The D-galactose is derived from lactose hydrolysate, which comprises galactose and glucose, two aldo-sugars which are difficult to separate. The galactose component is presently separated from the hydrolysate by column separation. The processes of chemical synthesis of D-tagatose and column separation of galactose are expensive, complicated and inefficient.

A current chemical process for synthesizing D-tagatose is described in U.S. Pat. No. 5,002,612. The process is carried out by isomerizing a mixture containing D-galactose with a metal hydroxide in the presence of an inorganic salt catalyst to form an intermediate metal hydroxide-D-tagatose complex. The intermediate then is neutralized with acid to yield D-tagatose.

The lack of suitable industrial methods for producing D-tagatose is recognized in the art as noted in Japanese patent disclosure 60-248196. The disclosure describes the production of D-tagatose from dulcitol by contacting a bacterial strain of the genus Arthrobacter with an aqueous solution containing dulcitol and recovering accumulated D-tagatose. This method has the disadvantage that dulcitol is not available in large quantities and is expensive. Moreover, the enzyme galactitol dehydrogenase requires NAD (nicotinimide-adenine dinucleotide) an expensive co-enzyme which makes the conversion of dulcitol to D-tagatose more costly.

Enzymatic methods for converting an aldose or aldose derivative to a ketose or ketose derivative are well known. The enzymatic conversion of glucose to fructose, for example, is widely practiced on a commercial scale. Enzymatic methods for converting D-galactose to D-tagatose, however, have not been developed until recently, as disclosed in the parent of this application.

The L-arabinose isomerase used according to the present invention is known for its use in the production of L-ribulose from L-arabinose. U.K. Patent Specification No. 1 497 888 (equivalent to U.S. Pat. No. 4,069,104) alleges that the conversion of D-galactose to D-tagatose using L-arabinose isomerase is known, but cites an unrelated reference (J. Biol Chem, 1071, 246, 5102–6) as a basis for the disclosure. No description of the conditions for such conversion are provided.

References having specific data concerning the activity of L-arabinose isomerase on D-galactose describe the activity as poor or undetectable. For example, D-galactose is reported as a poor substrate for propagating L-arabinose isomerase in a chapter entitled "L-Arabinose Isomerase" by K. Yamanaka and W. A. Wood, *Methods In Enzymology*, Vol. IX Carbohydrate Metabolism at 596–602 (Edited by Willis A. Wood, 1966). L-arabinose isomerase derived from *Lactobacillus gayonii* was found to have a high affinity for L-arabinose, but low affinity for D-galactose and D-fucose. The authors concluded that the isomerase had affinity for sugars with an L-cis hydroxyl configuration at C-3 and C-4. Id. at 602.

The activity of L-arabinose isomerase on D-galactose is further reported as "slight" in "Crystallization and Properties of L-Arabinose Isomerase From *Lactobacillus Gayonii*", Nakamatu, *Biochim. Biophys. Acta,* 178 (169) at 156–165. It is also described as a "slow" substrate for L-arabinose-L-ribulose-isomerase in "Degradation of L-Arabinose by Aerobacter Aerogenes", F. J. Simpson, *The Journal of Biological Chemistry,* 1958, Volume 230, pages 457–472.

A comparison of L-arabinose isomerases from *Mycobacterium smegmatis* induced by L-arabinose and D-galactose is reported by K. Izumori et al. in *Journal of Bacteriology*, January 1978 at 413–414. D-galactose was found to induce both an L-arabinose permease and an L-arabinose isomerase. The isomerase induced by D-galactose had similar properties to the L-arabinose induced isomerase. D-galactose was found to be suitable as a substrate of the permease, but not a substrate of the isomerase. Id. at 414.

Purified galactose is difficult to make because it must be separated from glucose, both aldo-sugars. Mixtures of D-galactose and D-glucose are produced when lactose is hydrolyzed by lactase. The lactose can be derived from cheese whey and/or milk. A method of preparing galactose from lactose is disclosed in U.S. Pat. No. 4,595,659 to Roland et al.

An excess of lactose is currently produced by the North American dairy industry as a by product of cheese manufacture, in the form of whey, whey permeate or milk permeate. These by-products are a potential source of food for both human and animal consumption and methods for using them are being sought. The enzymatic hydrolysis of lactose to glucose and galactose by beta-galactosidase (also referred to in this specification as lactase, beta-galactosidase being the systemic name for lactase), followed by fermentation, is described by J. R. Ernandes et al., "Simultaneous Utilization of Galactose and Glucose by Saccharomyces spp.", *Biotechnology Technique,* Vol. 6, No. 3, May/ June 1992, pp. 233–238. The authors describe a means of adapting yeast for galactose utilization to allow the simultaneous uptake of galactose and glucose, thereby overcoming the tendency of glucose to be utilized by yeast cells in preference to other sugars.

Other processes for using whey or lactose as fermentation substrates have been described in the literature. A process for co-fermenting ethanol from cheese whey and corn using fungal alpha-amylase is described by P. J. Whaler, "Development, Scale-up and a Continuous Fermentation Process for the Cofermentation of Cheese Whey and Corn for Ethanol Production," University of Nebraska, Lincoln, Nebr. 68583-0745 U.S.A., *Dissertation Abstracts International*, B1988, 49(4) 964–965.

The production of a fermented beverage using lactase hydrolyzed milk was reported by T. Miyamoto et al., *Japanese Journal of Dairy and Food Science*, 1986, 35(4) A143–A150. Whey and skim milk were incubated with beta-galactosidase from *Aspergillus oryzae*. The process gave 80–90% hydrolysis of lactose in whey and 40–50% hydrolysis in skim milk. Production of acid and ethanol by *Zymomonas mobilis*, ATCC 10,988, incubated in whey for 36 hours at 30° C. was very slight, but increased as the degree of lactose hydrolysis increased. Chromatographic analysis showed that glucose in the treated whey was almost completely utilized by *Z. mobilis* within 18 hours, but that galactose and lactose were hardly affected. Mixed cultures of *Z. mobilis* with various Streptococcus and Lactobacillus enzymes were found to increase acid production but did not increase the amount of ethanol produced by *Z. mobilis*, the maximum being 0.88% in lactose-hydrolyzed whey.

In a comparison of lactose-hydrolyzed whey and normal whey as substrates for alcohol production, galactose was found to be a poor substrate for alcohol production. V. S. O'Leary et al., "Influence of Lactose Hydrolysis and Solids Concentration on Alcohol Production by Yeast in Acid Whey Ultrafiltrate," *Biotechnology and Bioengineering*, Vol. XIX, pages 1689–1702 (1977). *Saccharomyces cerevisiae* and *Kluyveromyces fragilis* were tested. *S. cerevisiae* was found to give higher alcohol yields, but the process was deemed wasteful because galactose, which comprised about half the available carbohydrate, was not fermented.

The fermentation of glucose has been reported as a means of enriching fructose. A method of producing very enriched fructose syrup by selective conversion of glucose to ethanol using immobilized cells of *S. cerevisiae*, ATCC 36,859 (mutated culture), is described by D. W. Koren et al., "Continuous Production of Fructose Syrup and Ethanol from Hydrolysed Jerusalem Artichoke Juice," *Journal of Industrial Microbiology*, 7 (1991) pages 131–136. Some fructose was consumed and the glucose/fructose conversion rate ratio was regulated by the glucose concentration in the product stream. The same *S. cerevisiae* was used to produce sorbitol and ethanol from Jerusalem artichokes. Z. Duvnjak et al., "Production of Sorbitol and Ethanol from Jerusalem Artichokes by *Saccharomyces cerevisiae* ATCC 36859," *Applied Microbiology Biotechnology* (1991) 35:711–715. The sorbitol was produced from fructose following ethanol production from glucose.

None of the foregoing literature references or patents disclose or suggest an enzymatic process for isomerizing D-galactose to D-tagatose. Moreover, one skilled in the art would be taught away from using L-arabinose isomerase for the isomerization because the art describes the activity of the enzyme on D-galactose as poor.

SUMMARY OF THE INVENTION

It has now been found that D-tagatose can be manufactured from cheese whey and/or milk by employing biological fermentation and isomerization processes. According to the invention, lactose is derived from cheese whey and/or milk by conventional membrane processing to prepare a lactose permeate. The lactose permeate is hydrolyzed with lactase to make a lactose hydrolysate which comprises a mixture of galactose and glucose. The two aldo-sugars generally are present in about equal quantities. Galactose is separated from the glucose by selective fermentation of the glucose to ethanol and the galactose is then contacted with L-arabinose isomerase to produce D-tagatose.

One feature of the invention is the finding that galactose can be separated from a mixture of galactose and glucose by selective fermentation of the glucose to ethanol. A yeast and/or bacteria is employed which preferentially ferments glucose over galactose. Following fermentation, the galactose is separated from the fermentation broth and concentrated by evaporation. The concentrated galactose can be crystallized to make a purified galactose powder. The ethanol is recovered and can be concentrated by distillation or utilization of a pervaporation membrane system to produce 95% ethanol as a value added by-product. Suitable pervaporation systems are available from Zenon Environmental Inc., 845 Harrington Court, Burlington, Ontario L7N 3P3, Canada.

The invention provides a means for using lactose in an economic process for making purified galactose, a valuable intermediate product of the invention.

In a preferred embodiment, the lactose permeate is desalinated before it is hydrolyzed, or the lactose hydrolysate itself is desalinated. Salt is undesirable as a flavor component of galactose and D-tagatose. It is also undesirable because it inhibits crystallization.

Desalinated hydrolyzed lactose is a valuable intermediate made according to the invention. It has utility as a sweetener or flavorant in making chocolate, ice cream, pudding, confectionery products, cheese based products, frozen novelties, baked goods and the like.

Another feature of the invention is the finding that L-arabinose isomerase is an effective enzyme for the production of D-tagatose from D-galactose. In particular, L-arabinose isomerase can be used to produce D-tagatose from D-galactose under reaction conditions which can be optimized for isomerases derived from various microorganism strains.

The culture medium used to propagate cells for the production of L-arabinose isomerase is maintained at a controlled pH for enhanced production of the isomerase and optimum enzymatic activity. A pH from about 4.0 to about 9.0 should be maintained during propagation, and a pH from about 5.5 to about 7.0 is generally preferred.

The isomerase employed according to the invention can be used in whole-cell, cell free or immobilized systems. Effective isomerization to produce D-tagatose from D-galactose can be conducted in a continuous, semi-continuous or batch operation, consistent with the enzyme system employed.

As an option, productivity of the isomerase can be enhanced using metal ion activators.

Excellent yields of D-tagatose based on D-galactose are obtained when the D-galactose starting material is in high concentration due to the high Km value for D-galactose. (The Km value expresses the binding efficiency of the enzyme to the substrate.) When the starting materials have low concentrations of D-galactose, however, yields will vary depending on the microorganism used to prepare the enzyme. For commercial production of D-tagatose, it is preferable to employ relatively concentrated D-galactose, at least about 5% by weight, as a starting material. The preferred range of D-galactose concentration in the starting material is from about 10% to about 60% by weight. Of course, more concentrated D-galactose can be used, up to its maximum solubility in water (about 70% by weight D-galactose at about 25° C.).

All percentages recited throughout the specification and claims are by weight unless specified otherwise.

Figure 1:
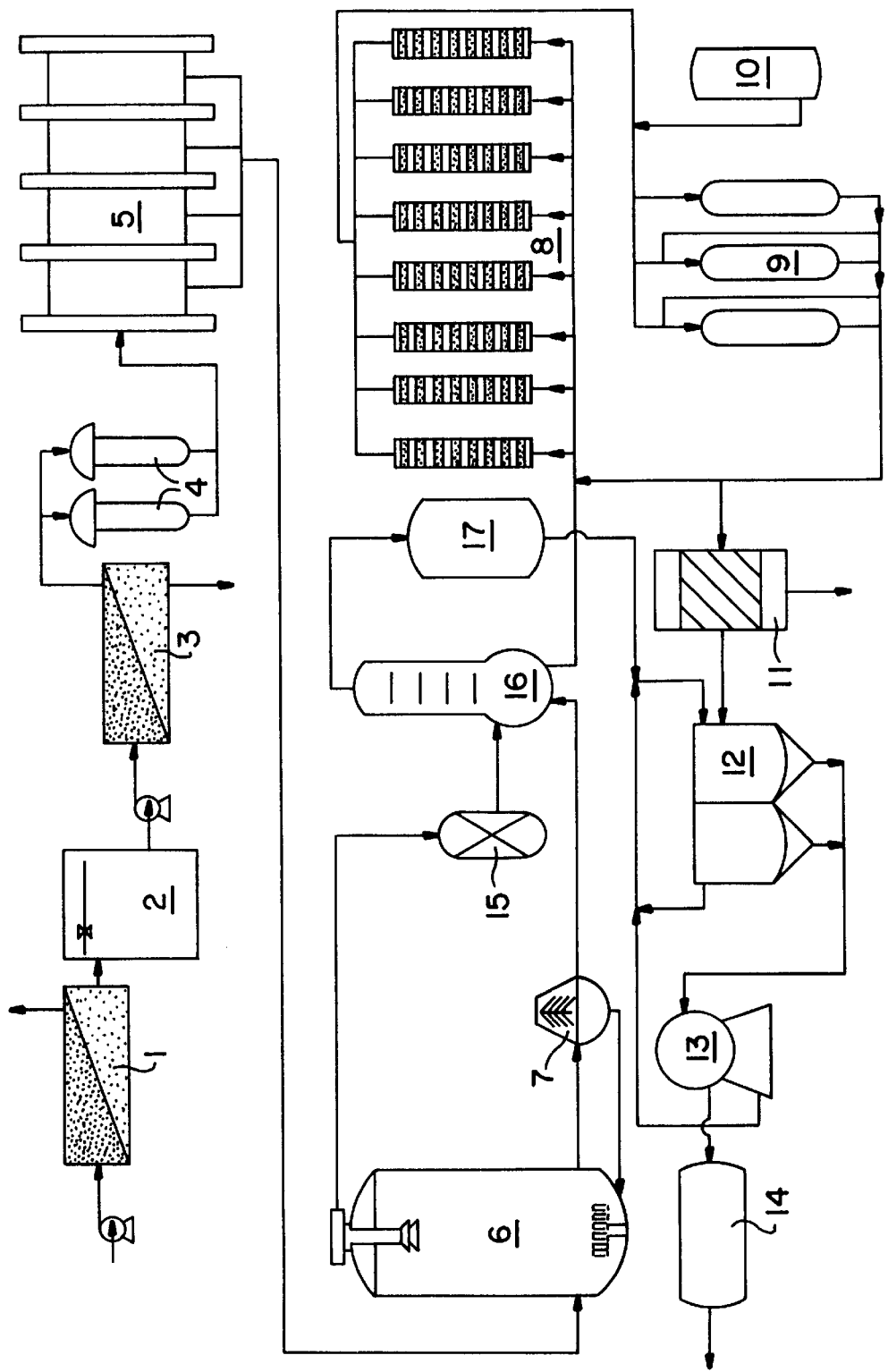
FIG. 1 is a flow diagram of a preferred process of the invention.

Lactose permeate is passed through ultrafiltration membrane 1 to remove protein. The reduced protein permeate then is supplied to feed tank 2 and pumped to reverse osmosis or nanofiltration membrane 3 for desalination and concentration. The desalinated concentrated permeate is supplied to microfilters 4 to separate remaining high molecular weight particles (bacteria, i.e. insoluble protein). Modules 5 containing membrane immobilized lactase enzyme are employed to hydrolyze the desalinated deproteinated lactose. A desalinated hydrolyzed lactose is thereby prepared as an intermediate which contains approximately equal amounts of glucose and galactose.

The desalinated hydrolyzed lactose is introduced into a semi-continuous fermenter 6 having submerged whole cells of yeast and/or bacteria. Ethanol produced by fermentation in fermenter 6 is removed by vacuum with vacuum pump 15 and concentrated by distillation in column 16. Ethanol is also removed from the fermentation media within the fermenter 6 by feeding the media into a centrifuge 7 where it is separated into a cell-free liquid stream which is sent to distillation column 16 and the cells are recirculated back to the fermenter 6. The distilled ethanol is stored in tank 17. Some of the distilled ethanol is employed in the D-tagatose crystallization process as explained below and the remainder is removed as a by-product.

The galactose rich stream from distillation column 16 is subject to isomerization to tagatose at columns 8. The galactose and D-tagatose mixture is absorbed on parallel cation exchange columns 9. The galactose and D-tagatose are selectively eluted utilizing eluant (deionized water) from tank 10. The D-tagatose fraction is concentrated in evaporator 11 and the galactose fraction is recycled to columns 8 to enhance isomerization efficiency. The concentrated D-tagatose can be used as is or it can be crystallized in crystallizers 12.

Crystallization in crystallizers 12 is enhanced by introducing ethanol with the D-tagatose and optionally seeding with D-tagatose crystals. Ethanol is separated from the crystallized D-tagatose by basket filter 13 and is recycled to crystallizers 12. The D-tagatose crystals are dried in dryer 14.

DETAILED DESCRIPTION OF THE INVENTION

A lactose permeate is prepared by ultrafiltration of cheese whey and/or milk. The lactose permeate has from about 2% to about 6% lactose, from about 0.2% to about 0.4% protein and from about 0.2% to about 0.6% salt. The remaining component of the permeate is primarily water with a trace of fat. The lactose permeate can be processed further at this stage or it can be spray dried to make a lactose concentrate powder. The powder is stable in storage and can be shipped inexpensively. If lactose concentrate powder is employed, however, it must be rehydrated before further processing according to the invention. Other starting materials which are suitable as lactose sources include concentrated sweet whey, sweet whey powder and lactose concentrate syrup.

In a preferred embodiment of the invention, the lactose permeate, or rehydrated lactose concentrate powder, is polished by ultrafiltration membrane 1 to reduce the concentration of protein and thereby avoid bacterial contamination in the succeeding processing steps. Any conventional membrane which can remove high molecular weight components can be employed. High molecular weight cutoff membranes such as regenerated cellulose and polysulfone manufactured by Millipore Corporation, Medford, Mass., are suitable for this purpose.

The reduced protein lactose permeate is desalinated by reverse osmosis or nanofiltration membranes 3. A suitable nanofiltration membrane is the MPT 10 membrane manufactured by Membrane Products Kiryat Weitzmann, Rehovat, Israel. While desalination is not essential to the overall process of manufacturing D-tagatose as disclosed in this specification, it is preferred because salt has an undesired taste in the products of the invention and it inhibits crystallization of the D-tagatose. Desalination can be carried out at other stages of the process rather than at this stage, for example, before protein content is reduced, after the lactose is hydrolyzed or before the permeate is spray dried.

Following desalination, the lactose permeate can be subject to microfiltration at microfilters 4, or other suitable filtration, to reduce microbial contamination and foreign particles such as insoluble protein. Suitable microfilters include cellulose ester and PVDS (polyvinylidene fluoride) having a pore size within the range of from about 0.2 to about 0.4 microns. Suitable membranes are available from Millipore Corporation. Then the permeate is hydrolyzed with lactase at modules 5.

Hydrolysis can be carried out by conventional means on a continuous, semi-continuous or batchwise basis, consistent with the particular lactase employed. The lactase can be any conventional lactase such as those derived from Aspergillus sp. Suitable lactases are Biolactase, available from Quest International, Sarasota, Fla., and Takamine Brand fungal lactase available from Solvay Enzymes Inc., Elkhart, Ind. Optimum hydrolysis reaction conditions will vary depending upon the lactase employed. Generally, however, hydrolysis should be conducted at a temperature from about 40° C. to about 60° C. and a pH from about 4 to about 6. In a preferred embodiment of the invention the lactase is membrane immobilized for use in a continuous process. A preferred system is sold under the designation ACTIMOD by Biosupport Materials, Pinebrook, N.J., a division of FMC Corporation.

The hydrolyzed lactose can be concentrated, for example in an evaporator, to yield a solution which generally comprises from about 2% to about 20% galactose and from about 2% to about 20% glucose, wherein the galactose and glucose concentrations generally are about equal. The remaining components primarily are low concentrations of protein, salt, fat and residual unhydrolysed lactose.

The concentrated hydrolyzed lactose is fermented with yeast or bacteria under fermentation conditions to ferment selectively the glucose to ethanol. Fermentation can be carried out on a continuous, semi-continuous or batchwise basis consistent with the yeast or bacteria employed. When a bacteria is employed, for example, it can be immobilized in columns and the fermentation can be carried out on a continuous basis. In this case, the galactose and ethanol leaving the columns can be separated by distillation of the ethanol.

Suitable yeasts and bacterias for use according to the invention are those which effectively ferment glucose to ethanol and which are relatively ineffective to ferment galactose, particularly when glucose is present. Yeasts which can be employed according to the invention include *Saccharomyces cerevisiae*, such as ATCC 287 and ATCC 561. Bacteria cultures which can be employed, subject to regulatory approval, include *Zymomonas mobilis*, such as ATCC 10,988 and ATCC 31,822.

When yeast, bacteria, or a combination of yeast and bacteria is used for fermentation, the fermentation medium generally is comprised of lactose hydrolysate (a mixture of about 2–20% glucose and 2–20% galactose wherein the glucose and galactose are present in approximately equal concentrations), and about 0.1% ammonium phosphate as a nitrogen/phosphate source. Fermentation pH is maintained at from about 4.5 to about 5.5 using ammonium hydroxide and the temperature is controlled at from about 25° C. to about 35° C.

In a preferred embodiment of the invention, a whole-cell S. cerevisiae yeast is introduced into a semi-continuous fermenter 6 containing sufficient lactose hydrolysate to keep the whole cells submerged. Fermentation is continued for a sufficient time to consume the glucose present in the production of ethanol. The glucose level is monitored by a suitable analytical technique such as HPLC or a glucose analyzer. The fermentation is terminated as soon as glucose is consumed (fermented to ethanol and carbon dioxide). Some ethanol is removed during fermentation by vacuum pump 15 and distilled in column 16 to make 95% ethanol as a by-product which can be stored in tank 17.

Following fermentation, the galactose and ethanol mixture is separated from the whole-cells by centrifugation in centrifuge 7. (Alternatively, the whole cells could be removed by a microfiltration membrane system.) The whole cells are returned to the fermenter 6 and the galactose and ethanol mixture is fed to distillation column 16 to remove ethanol. An alternative means for ethanol recovery is pervaporation utilizing a pervaporation membrane system. A suitable system is available from Zenon Environmental Inc. as noted earlier in this specification. The galactose-rich stream from distillation column 16 is subject to isomerization to tagatose at columns 8.

The D-galactose is isomerized to D-tagatose using L-arabinose isomerase under conditions which can be optimized by those skilled in the art based on the present disclosure.

L-arabinose isomerase can be derived from various microorganisms using a culture medium containing the pentose sugar L-arabinose. Reported sources of the enzyme include *Lactobacillus pentosus, Lactobacillus fermentum* (previously known as *Lactobacillus gayonii*), *Lactobacillus mannitopous, Lactobacillus buchneri, Lactobacillus brevis, Lactobacillus pentoaceticus, Lactobacillus lycopersici, Aerobacter aerogenes, Bacillus amyloliquefaciens, Bacillus subtilis, Candida utilis, Clostridium acetobutylicum, Escherichia coli, Erwinia cativosa*, and Pediococcus organisms such as *Pediococcus pentosaceous*. We have also found that Arthrobacter sp. can be used to produce L-arabinose isomerase. Many of these microorganisms are suitable for culturing enzymes which can be used in foods.

The culture medium used to propagate cells for the production of L-arabinose isomerase is maintained at a controlled pH from about 4.0 to about 9.0, and should be maintained at a controlled pH from about 5.5 to about 7.0 for optimum results. The temperature of the culture medium should be maintained at from about 30° C. to about 40° C. during propagation. Moreover, the L-arabinose sugar must be used as a carbon source for the propagation because L-arabinose isomerase is an inducible enzyme.

Following propagation, the cell mass is harvested and washed with a buffer at a pH from about 5.0 to about 7.5, and preferably from about 6.0 to about 7.0. Suitable buffers include phosphate, maleate and TRIS (trizma base, or tres (hydroxomethyl)aminomethane). The buffer pH preferably should be the same as the pH of the culture medium.

L-arabinose isomerase is an intracellular enzyme and, therefore, must be extracted from the harvested cells. This task can be accomplished with the aid of lysozyme, by sonication, or by other conventional means. The extracted enzyme can be separated from the cell debris by filtration or centrifugation. If desired, the L-arabinose isomerase solution then can be evaporated to form a stable concentrate.

The activity of L-arabinose isomerase can be assayed based on the appearance of keto-pentose (L-ribulose) or keto-hexose (D-tagatose) after incubation in the presence of the substrate aldo-pentose (L-arabinose) or aldo-hexose (D-galactose), respectively. The keto-pentose or keto-hexose can be measured colorimetrically utilizing cysteine-carbazole sulfuric acid as a reagent. The cysteine-carbazole method is described in, Zacharias Dische, "Color Reaction of Ketoses with Carbazole and Sulfuric Acid", *Methods in Carbohydrate Chemistry* (1962) page 481 [132]. Samples should be analyzed in duplicate, utilizing one sample as a blank to correct for substances which may interfere with the calorimetric ketose determination.

For purposes of this specification, one unit of L-arabinose isomerase activity is defined as that amount of enzyme which is required to produce one micromole of L-ribulose or D-tagatose from the respective substrates, L-arabinose or D-galactose, following ten minutes of incubation under assay conditions.

L-arabinose isomerase can be used in various conventional forms for the isomerization of D-galactose to D-tagatose. Successful results have been achieved using whole-cells, cell-free extracts and immobilized enzyme. Production of D-tagatose can be carried out effectively using continuous, semi-continuous or batch systems.

Optimum isomerization temperature and pH conditions will vary depending on the microorganism strain used to prepare the enzyme. Best results generally have been achieved at temperatures from about 20° C. to about 80° C. and preferably from about 50° C. to about 70° C., and at a pH from about 4.0 to about 9.0 and preferably from about 5.5 to about 7.0. Isomerization temperatures as high as 100° C. can be used with highly thermostable isomerases derived from mutant strains. When one operates within the preferred ranges of galactose concentration, from about 10 to about 60% by weight; temperature, from about 50° C. to about 70° C.; and pH, from about 5.5 to about 7.0, it is possible to achieve a yield of D-tagatose within the range of from about 20% to about 45% by weight based on starting galactose.

Productivity of the isomerase can be enhanced using metal ion activators. Suitable ions include manganese, magnesium, ferric, ferrous, cobalt, calcium and zinc. The selected ion and optimum ion concentration for a given L-arabinose isomerase will vary based on the microorganism used as a source of L-arabinose isomerase. When D-tagatose is being produced for food applications, however, certain ions such as cobalt must not be used.

The concentration of the D-galactose can have a substantial impact on the rate and yield of D-tagatose based on D-galactose. This phenomenon was observed when the enzyme was derived from *Lactobacillus pentosus, Bacillus subtilis* and Arthrobacter sp. Low concentrations of D-galactose in the range from about 0.1% to about 1% by weight of the substrate, resulted in low rates and yields of D-tagatose. When D-galactose is present in a concentration of at least about 5% by weight and preferably at least about 10% by weight, however, rates and yields were excellent as illustrated by the examples later in this specification.

The stream leaving columns 8 contains galactose and D-tagatose and they are separated by cation-exchange chromatography at columns 9. The galactose and D-tagatose are selectively eluted utilizing eluant (deionized water) from tank 10.

As an option, the galactose can be concentrated by evaporation or other suitable means before isomerization and/or it can be purified by passing it through a cation exchange resin. Then it can be concentrated further under vacuum if desired. Other options for concentrating or purifying the galactose will be apparent to those skilled in the art. Concentrated galactose can be crystallized if desired by conventional means.

Most of the D-tagatose is concentrated in evaporator 11 and the remaining portion is recycled to columns 8 to enhance isomerization efficiency. The concentrated D-tagatose can be used as is or it can be crystallized in crystallizers 12.

Crystallization of the D-tagatose in crystallizers 12 can be made more efficient by adding ethanol to remove water and enhance crystal formation. The crystallization temperature is preferably maintained at from about 0° C. to about 5° C. with a jacket and cold water. D-tagatose crystals optionally can be used to seed the crystallization.

After the D-tagatose is crystallized, ethanol is separated by conventional means. A basket filter 13 is suitable for this purpose. Separated ethanol is recycled to the crystallizers 12 and the D-tagatose crystals are dried in a conventional dryer, such as drum dryer 14. The dried D-tagatose crystals generally contain less than about 1% galactose and have less than about 1% free moisture.

EXAMPLES

Example 1

A pure culture of *Lactobacillus pentosus*, ATCC 8041, was obtained. The organism was gram positive, non spore forming and microaerophilic.

The *Lactobacillus pentosus* (stock culture) was maintained as a lyophilized (freeze dried) culture. To initiate the fermentation process, a lyophile vial was opened and the pellet transferred into a 250 milliliter Erlenmeyer flask containing 100 milliliters of a medium having the following composition:

| Component | % by Weight |
| --- | --- |
| Dextrose | 2 |
| Peptone | 1 |
| Yeast Extract | 0.4 |
| Potassium phosphorous diebasic | 0.2 |
| Sodium acetate | 0.5 |
| Triamonium citrate | 0.02 |
| Magnesium Sulfate | 0.2 |
| Manganese sulfate | 0.005 |

The medium was sterilized at 121° C. for 20 minutes. The inoculated flask was incubated at 37° C. on a rotary shaker at 200 rpm for 24–48 hours while pH was maintained at 6.8. Propagated cells were harvested by centrifugation under sterile conditions. The supernatant was removed and the suspended cell mass was maintained in the same broth used for fermentation. Sterile harvested cells were suspended into a fresh sterile medium having the same composition as above and further containing 10% (vol./vol.) glycerol as a protective agent. The cell suspension was then dispensed into cryogenic vials and stored in a −70° C. freezer. These cryogenic vials were used as working vials for fermentation experiments and enzyme production.

For L-arabinose isomerase production, the culture was propagated in two stages.

In the inoculum stage, a 250 milliliter Erlenmeyer flask containing 100 milliliters of sterile BYF-100 medium was inoculated with a *Lactobacillus pentosus* culture taken from one of the cryogenic vials. (BYF-100 is a partially hydrolysed yeast available from Universal Foods Corporation, Milwaukee, Wis.) After inoculation, the flask was incubated on a shaker for 30 hours at 37° C. and 200 rpm.

For the enzyme production stage, the inoculum stage flask (100 milliliters propagated cells) was used to inoculate a 2 liter glass fermenter containing one liter sterile BYF 100 medium. The fermenter was operated at a temperature of 37° C. with agitation at 200 rpm and aeration at 0.5 liters per minute. (0.5:1 volume/volume based on fermentation media volume). Fermentation pH was controlled at 6.5 using a 2N sterile sodium hydroxide.

| BYF 100 MEDIUM | |
| --- | --- |
| Component | % by Weight |
| BYF - 100 | 2.1 |
| sodium acetate | 1.0 |
| magnesium sulfate | 0.02 |
| potassium phosphate (mono) | 0.02 |
| ferrous sulfate | 0.001 |
| manganese sulfate | 0.001 |
| sodium chloride | 0.001 |
| L-arabinose[1,2] | 1.2 |
| D-glucose[2] | 0.3 |

[1]Previously published data taken from Nakamatu, T. and Yamanaka, K., Crystallization and Properties of L-Arabinose Isomerase From Lactobacillus and Gayonii, Biochim. Biophys. Acta. 178 (1969) 156–165 is shown for propagation in the absence of partially hydrolyzed yeast and with pH control.
[2]Sterilized separately by autoclaving or by microfiltration.

[1]Previously published data taken from Nakamatu, T. and Yamanaka, K., Crystallization and Properties of L-Arabinose Isomerase From Lactobacillus and Gayonii, Biochim. Biophys. Acta. 178 (1969) 156–165 is shown for propagation in the absence of partially hydrolyzed yeast and without pH control.
[2]Sterilized separately by autoclaving or by microfiltration.

Following 24 hours of propagation, the cell mass was harvested and washed with a phosphate or maleate buffer at pH 6.5. The L-arabinose isomerase was extracted from the harvested cells by sonication.

Cell mass and enzyme activity according to the present invention compares with previously published data as follows:

| | Published Data | Present Invention Data |
| --- | --- | --- |
| propagation age | 24 hours | 24 hours |
| propagation temp. | 37° C. | 37° C. |
| cell mass | 1.5 g/L. | 10.0 g/L. |
| activity (10 min.) | | |
| L-arabinose | 350 u/g. | 425 u/g. |
| D-galactose | — | 45 u/g. |
| total activity | | |
| L-arabinose | 525 u/L. | 4,220 u/L. |
| D-galactose | — | 395 u/L. |

Example 2

A comparative experiment was conducted to illustrate the effect of pH control on cell mass and enzyme yield activity. The same *Lactobacillus pentosus* as used in Example 1 was employed. Medium #1 of Example 3 was employed for enzyme production. Cells were harvested after 24 hours. The results are tabulated below:

| pH (Final) | Cells grams/liter | Activity units/gram | total |
|---|---|---|---|
| 5.1 (no buffer) | 1.7 | 284.0 | 482.8 |
| 6.5 (NaOH buffer) | 2.2 | 552.2 | 1214.8 |

Activity was assayed based on L-arabinose as a substrate.

Example 3

A media study was carried out to illustrate the effect of using partially hydrolysated yeast (BYF-100) instead of the more expensive yeast extract and nutrient both. The same *Lactobacillus pentosus* was used as in Example 1 and pH was controlled at 6.8 using 2N sodium hydroxide. Cells were recovered after 24 hours.

Media ingredients were as follows:

| COMPONENT | MEDIUM #1 (%) | MEDIUM #2 (%) |
|---|---|---|
| Yeast Extract | 0.4 | — |
| Nutrient Broth | 1.0 | — |
| BYF 100 | — | 2.1 |
| Sodium Acetate | 1.0 | 1.0 |
| Magnesium Sulfate | 0.02 | 0.02 |
| Potassium Phosphate | 0.02 | 0.02 |
| Sodium Chloride | 0.001 | 0.001 |
| Ferrous Sulfate | 0.001 | 0.001 |
| Manganese sulfate | 0.001 | 0.001 |
| L-arabinose | 1.0 | 1.0 |
| D-glucose | 0.3 | 0.3 |

Cell mass and activity were as follows:

| MEDIUM | AGE/HOUR | CELL MASS (g./L.) | ACTIVITY (U/g.) | TOTAL ACTIVITY (U/L. medium) |
|---|---|---|---|---|
| #1 | 24 | 4.2 | 430 | 1,806 |
| #2 | 24 | 10.2 | 552 | 5,630 |

Activity was assayed based on L-arabinose as a substrate.

Example 4

Cell propagation was carried out using *Lactobacillus pentosus* as described in Example 1 except that pH was maintained at 6.8 using 2N sodium hydroxide. The cells were harvested, washed with a maleate buffer at pH 6.8 and centrifuged in two sequential stages. Harvested cell mass was weighed and portions were selected for use in bioconversion of D-galactose to D-tagatose using a whole-cell process, a cell free process and an immobilized enzyme process. A 30% by weight D-galactose substrate was used having 0.01 M Fe++ (based on $FeCl_2$) and a maleate buffer was employed to maintain the pH at 6.8.

Whole-Cell Process

Approximately 10 and 40% w/w wet weight cells was placed into two test tubes each containing 4 ml. of 30% w/w D-galactose substrate. The test tubes were placed in a water bath at 60° C. A test tube containing 4 ml. D-galactose substrate without cell mass also was placed in the same water bath as a blank sample. Samples were taken periodically, centrifuged, and analyzed for D-tagatose concentration by the colorimetric method using cysteine carbazole as follows:

D-tagatose Assay

To 1.0 ml of the bioconversion reaction medium (using a dilution factor if needed) the following is added:

0.2 ml of cystein hydrochloride (1.5% in water);

6.0 ml 75% sulfuric acid (450 ml conc. sulfuric acid+190 ml water); and 0.2 ml of 0.12% alcohol solution of carbazole (0.12 gram carbazole in 100 ml 95% ethanol).

The test tubes are incubated for 10 minutes at 57° C. and optical density (O.D.) is read at 540. The D-galactose substrate is used as a blank for reference.

The samples were also analyzed by high pressure liquid chromatography (HPLC) for D-tagatose and D-galactose concentration as a confirmatory test.

The results are tabulated below:

Bioconversion conditions:
30% D-galactose+0.01 M $FeCl_2$
Bioconversion pH 6.8
Bioconversion temp. 60° C.

| | | 40% Cell Mass | | 10% Cell Mass | |
|---|---|---|---|---|---|
| Age/Hour | | % D-tagatose | % Bioconv | % D-tagatose | % Bioconv |
| 24 | | 5.3 | 17.7 | 2.3 | 7.7 |
| 48 | | 7.2 | 24.0 | 3.8 | 12.7 |
| 72 | | 8.1 | 27.0 | 4.7 | 15.7 |
| 96 | | 8.5 | 28.3 | 4.8 | 16.0 |
| 115 | | 9.5 | 32.0 | 5.0 | 17.0 |
| 144 | | 11.6 | 38.7 | 5.6 | 18.6 |
| 168 | | 11.9 | 39.7 | 5.8 | 19.3 |

Cell-Free Process

Approximately 1 gram wet weight cells was suspended in 2 ml. maleate buffer pH 6.8 and sonicated for 15 minutes at low temperature. The cell extract was added to the D-galactose substrate in a test tube, and the test tube was placed in two separate water baths, one at 50° C. and the other at 60° C. Another test tube containing the D-galactose substrate without cell extract was placed in each of the two water baths as a blank.

Samples were taken periodically, centrifuged, and analyzed by the calorimetric method and HPLC as described above for whole-cell bioconversion.

The results are tabulated below:

| Bioconversion conditions: | |
|---|---|
| D-galactose | 0.01M (1.8%) |
| $MnCl_2$ | 0.005M |
| temperature | 50° C.–60° C. |
| pH | 7.0 |

| | 50° C. Water Bath | | 60° C. Water Bath | |
|---|---|---|---|---|
| Age/Hour | % D-tagatose | % Bioconv | % D-tagatose | % Bioconv |
| 0 | 0.0 | 0.0 | 0.0 | 0.0 |
| 18 | 0.52 | 29.0 | 0.74 | 41.0 |
| 24 | 0.73 | 40.6 | 0.77 | 42.8 |
| 40 | 0.77 | 42.8 | 0.79 | 43.9 |

Immobilized Enzyme

Untreated and glutaraldehyde treated activated microporous plastic-silica sheets manufactured by FMC corp. were evaluated for immobilization of whole-cells and cell-free extract of *Lactobacillus pentosus*. The glutaraldehyde treated membrane had a higher binding efficiency for both whole-cells and cell-free extract.

A 500 ml. volume of cell-free extract in maleate buffer at pH 6.8 and having a total activity of 3,720 units (D-tagatose units/10 min. incubation at 60° C.) was pumped through an immobilization reactor at a flow rate of 25 ml./min. for 16 hours at 4° C.

After immobilization, the reactor was flushed with maleate buffer at pH 6.8 to remove any free enzyme. Effluent was assayed and showed a total activity residue of 780 units, indicating that 2,940 units had been immobilized.

Five hundred milliliters of the D-galactose substrate was pumped through the immobilized enzyme reactor for one hour at 4° C., to saturate the enzyme with the substrate. The temperature then was raised to 60° C. for bioconversion.

The substrate pumping rate during bioconversion was 25 ml./min.

The reactor was evaluated periodically by measuring the degree of bioconversion of D-galactose to D-tagatose. After the first cycle was completed, fresh substrate was passed through the reactor as a second cycle.

The results are tabulated below:

|  | 1st Cycle | | 2nd Cycle | |
| --- | --- | --- | --- | --- |
| Age/Hour | % D-tagatose | % Bioconv | % D-tagatose | % Bioconv |
| 0 | 0 | 0 | 0 | 0 |
| 2 | 0.47 | 2.5 | 0.19 | 1.1 |
| 4 | 0.83 | 4.8 | 0.35 | 2.0 |
| 6 | 1.17 | 6.7 | 0.59 | 3.4 |
| 8 | 1.53 | 8.8 | 0.75 | 4.4 |
| 10 | 1.66 | 9.6 | 0.83 | 4.7 |
| 22 | 3.11 | 17.9 | 1.24 | 7.2 |
| 30 | 3.44 | 19.9 | 1.38 | 8.0 |
| 49 | 4.00 | 23.1 | 1.70 | 9.8 |
| 60 | 4.74 | 27.4 | 2.29 | 13.2 |
| 72 | — | — | 2.90 | 16.3 |

Example 5

Temperature sensitivity of L-arabinose isomerase derived from *Lactobacillus pentosus* was demonstrated by conducting bioconversions on 0.1 M L-arabinose and 0.2 M D-galactose and incubating for 10 minutes at 25° C. and again at 60° C. The results were as follows:

| Temperature | L-arabinose | D-galactose | Enzyme Activity Ratio (L-arabinose:D-galactose) |
| --- | --- | --- | --- |
| 35° C. | 24.6 u/ml. | 0.07 u/ml | 300:1 |
| 60° C. | 68.1 u/ml. | 0.90 u/ml | 85:1 |

The foregoing data shows that the bioconversion of D-galactose to D-tagatose by L-arabinose isomerase is more efficient at high temperatures.

Example 6

A series of bioconversions were conducted with varied parameters to determine optimum conditions for *Lactobacillus pentosus* L-arabinose isomerase. The results were as follows:

|  | Optimum | % Activity | Range | % Activity |
| --- | --- | --- | --- | --- |
| pH | 5.5–7.0 | 100 | 4.0–8.5 | 5–25 |
| Temperature | 65–70° C. | 100 | 30–80° C. | 4–0 |
| Activators | None | 100 | — | — |
|  | Cobalt | 200 |  |  |
|  | Ferrous[3] | 200 | 1 MM–10 MM | 123–250 |
|  | Manganese | 177 |  |  |
|  | Calcium | 143 |  |  |
|  | Magnesium | 141 |  |  |
|  | Zinc | 110 |  |  |
| D-galactose | 30% | 100 | 0.18–60 |  |

[3]Ferrous ion was selected as an activator for the bioconversion of D-galactose to D-tagatose because it is acceptable to the FDA as a food ingredient. Cobalt ion is not approved by the FDA for use in food processing.

[3]Ferrous ion was selected as an activator for the bioconversion of D-galactose to D-tagatose because it is acceptable to the FDA as a food ingredient. Cobalt ion is not approved by the FDA for use in food processing.

Example 7

*Bacillus amyloliquefaciens* (previously known as *Bacillus subtilis*, IFO 3022, was evaluated as a source of L-arabinose isomerase. Cells of the culture were propagated on the same medium as used in Example 1 in the presence of L-arabinose as a carbon source. Optimum pH, temperature, metal ion and metal ion concentration were evaluated as summarized below.

In the following tests, sample B was comprised of 0.8 ml. D-galactose and 0.2 ml. water and sample X was comprised of 0.8 ml. D-galactose an 0.2 ml. enzyme. The dilution factor for the optical density (O.D.) reading was 200×. (The cystein carbazole method was used for the D-tagatose assay.)

1) pH profile:

| (1.67 M D-Galactose, 0.01 M FeCl$_2$, 60° C., 120 min.) | | | |
| --- | --- | --- | --- |
| pH | SAMPLE | O.D. (540) | O.D. (X − B) |
| 4.0 | B | 0.7048 | — |
|  | X | 0.7328 | 0.019 |
| 4.5 | B | 0.7644 | — |
|  | X | 0.7978 | 0.0334 |
| 5.0 | B | 0.7009 | — |
|  | X | 0.7966 | 0.0957 |
| 5.5 | B | 0.8798 | — |
|  | X | 1.0498 | 0.1700 |
| 6.0 | B | 0.8179 | — |
|  | X | 1.3371 | 0.5192 |
| 6.5 | B | 0.8758 | — |
|  | X | 1.4310 | 0.5552 |
| 7.0 | B | 0.8471 | — |
|  | X | 1.6531 | 0.8060 |
| 7.5 | B | 0.8591 | — |
|  | X | 1.5910 | 0.7319 |
| 8.0 | B | 1.1146 | — |
|  | X | 1.5911 | 0.4765 |
| 8.5 | B | 1.4395 | — |
|  | X | 1.6379 | 0.1984 |
| 9.0 | B | 1.5178 | — |
|  | X | 1.5267 | 0.0089 |

2) Temperature profile:

| (1.67 M D-galactose, 0.01 M FeCl$_2$, pH 7.0, 120 min.) | | | |
|---|---|---|---|
| TEMPERATURE | SAMPLE | O.D. (540) | O.D. (X − B) |
| 20° C. | B | 0.6514 | — |
|  | X | 0.7331 | 0.0817 |
| 30° C. | B | 0.6521 | — |
|  | X | 0.7557 | 0.1036 |
| 40° C. | B | 0.6372 | — |
|  | X | 0.9307 | 0.2935 |
| 50° C. | B | 0.7778 | — |
|  | X | 1.1594 | 0.3816 |
| 60° C. | B | 0.6475 | — |
|  | X | 1.3163 | 0.6688 |
| 65° C. | B | 0.6836 | — |
|  | X | 1.4618 | 0.7782 |
| 70° C. | B | 0.7479 | — |
|  | X | 0.9103 | 0.1651 |
| 80° C. | B | 0.9098 | — |
|  | X | 0.9233 | 0.0135 |

3) Metallic ions:

| (1.67 M D-galactose, 0.005 M metallic ion, 60° C., 120 min.) | | | | |
|---|---|---|---|---|
| METALLIC ION | SAMPLE | O.D. (540) | O.D. (X − B) | D-TAGATOSE (M) |
| None | B | 0.6951 | — | — |
|  | X | 1.0661 | 0.3710 | 0.017 |
| Manganese | B | 0.8566 | — | — |
|  | X | 0.9552 | 0.7610 | 0.035 |
| Magnesium | B | 0.8504 | — | — |
|  | X | 0.9552 | 0.1048 | 0.005 |
| Ferric | B | 0.8213 | — | — |
|  | X | 1.2030 | 0.3817 | 0.018 |
| Ferrous | B | 0.9519 | — | — |
|  | X | 1.3957 | 0.4438 | 0.020 |
| Cobalt | B | 0.9189 | — | — |
|  | X | 1.0159 | 0.0970 | 0.005 |
| Calcium | B | 0.9782 | — | — |
|  | X | 1.1584 | 0.1802 | 0.009 |
| Zinc | B | 0.8826 | — | — |
|  | X | 1.0422 | 0.1596 | 0.007 |

4) Manganese ion at different concentrations:

| (1.67 M D-galactose, Mn ion different conc., 60° C., 120 min.) | | | | |
|---|---|---|---|---|
| MANGANESE ION (M) | SAMPLE | O.D. (540) | O.D. (X − B) | D-TAGATOSE (M) |
| 0.000 | B | 0.6182 | — | — |
|  | X | 1.0140 | 0.3958 | 0.018 |
| 0.001 | B | 0.6457 | — | — |
|  | X | 1.4180 | 0.7723 | 0.036 |
| 0.003 | B | 0.6967 | — | — |
|  | X | 1.3408 | 0.6441 | 0.030 |
| 0.005 | B | 0.6635 | — | — |
|  | X | 1.3450 | 0.6815 | 0.031 |
| 0.007 | B | 0.6663 | — | — |
|  | X | 1.3341 | 0.6678 | 0.031 |
| 0.009 | B | 0.7169 | — | — |
|  | X | 1.3760 | 0.6591 | 0.030 |
| 0.011 | B | 0.6664 | — | — |
|  | X | 1.3671 | 0.7007 | 0.032 |
| 0.013 | B | 0.7062 | — | — |
|  | X | 1.3913 | 0.6851 | 0.032 |

When the bioconversion tests were conducted using a 10% w/w D-galactose substrate with various metallic ions while pH was maintained at 7.0 with a maleic acid buffer. The results were as follows:

| SAMPLE[4] | METALLIC ION | TIME (HR) | % D-GALACTOSE | % D-TAGATOSE | % BIO-CONV. |
|---|---|---|---|---|---|
| B | 0.01 Mn$^{++}$ | 0 | 9.1 | 0.0 | — |
| X | " | 6 | " | 0.5 | 5.5 |
| X | " | 24 | " | 3.1 | 34.0 |
| X | " | 48 | " | 2.9 | 32.0 |
| B | 0.005 Fe$^{++}$ | 0 | 9.4 | 0.0 | — |
| X | " | 6 | " | 0.8 | 8.5 |
| X | " | 24 | " | 1.7 | 18.1 |
| X | " | 48 | " | 1.4 | 14.9 |
| B | 0.005 Co$^{++}$ | 0 | 9.5 | 0.0 | — |
| X | " | 6 | " | 0.9 | 9.5 |
| X | " | 24 | " | 2.6 | 27.4 |
| X | " | 48 | " | 3.0 | 31.6 |
| B | Mn$^{++}$,Fe$^{++}$,Co$^{++}$ | 0 | 9.7 | 0.0 | — |
| X | " | 6 | " | 0.6 | 6.2 |
| X | " | 24 | " | 1.0 | 10.3 |
| X | " | 48 | " | 0.7 | 7.2 |

The maximum bioconversion was 34.0%
[4]Sample B comprised 1.0 ml. substrate and 2.0 ml. water and sample X comprised 1.0 ml. substrate and 2.0 ml. enzyme. Each mixture was incubated at 50° C.

[4]Sample B comprised 1.0 ml. substrate and 2.0 ml. water and sample X comprised 1.0 ml. substrate and 2.0 ml. enzyme. Each mixture was incubated at 50° C.

Example 8

The following bacteria and actinomycetes which are capable of utilizing pentoses as a carbon source and known to produce the enzyme xylose isomerase were evaluated for the production of the enzyme L-arabinose isomerase.

| Ampullariella sp. | ATCC 31354 |
| Bacillus licheniformis | ATCC 31604 |
| Arthrobacter sp. | ATCC 21920 |
| Streptomyces flaveus | ATCC 21947 |
| Streptomyces wedmorensis | ATCC 21230 |
| Streptomyces olivochromogenus | ATCC 21715 |

The cultures were screened based on cell propagation on medium #1 of Example 3 in the presence of L-arabinose as a carbon source.

Results showed Arthrobacter sp. ATCC 21920 to be an effective source L-arabinose isomerase. This observation was confirmed several times by calorimetric enzyme assay and D-tagatose detection by high performance liquid chromatography.

Average cell mass produced by this culture was 1.5 g per 100 ml. propagation medium, with L-arabinose isomerase activity of 21 U/g/10 min. incubation using D-galactose as a substrate.

Example 9

Cells of Arthrobacter sp. ATCC 21920 were propagated on medium #1 of Example 3 in the presence of L-arabinose as a carbon source. Optimum pH, temperature, metal ion and metal ion concentration were evaluated on the cell extract containing L-arabinose isomerase as summarized below.

In the following tests, sample B was comprised of 0.8 ml. D-galactose and 0.2 ml. water and sample X was comprised of 0.8 ml. D-galactose and 0.2 ml. enzyme. The dilution factor for the optical density (O.D.) reading was 200×.

1) pH profile:

| (1.67 M D-galactose, 0.01 M FeCl₂, 60° C., 120 min.) | | | |
|---|---|---|---|
| pH | SAMPLE | O.D. (540) | O.D. (X − B) |
| 4.0 | B | 0.6118 | — |
|  | X | 0.6057 | 0.00 |
| 4.5 | B | 0.7076 | — |
|  | X | 0.7504 | 0.04 |
| 5.0 | B | 0.6936 | — |
|  | X | 0.8063 | 0.11 |
| 5.5 | B | 0.7244 | — |
|  | X | 0.9081 | 0.18 |
| 6.0 | B | 0.7286 | — |
|  | X | 1.6741 | 0.95 |
| 6.5 | B | 0.8259 | — |
|  | X | 2.0338 | 1.21 |
| 7.0 | B | 0.8536 | — |
|  | X | 2.2248 | 1.37 |
| 7.5 | B | 0.8317 | — |
|  | X | 1.7471 | 0.92 |
| 8.0 | B | 0.7212 | — |
|  | X | 1.3700 | 0.65 |
| 8.5 | B | 0.7704 | — |
|  | X | 1.2029 | 0.43 |
| 9.0 | B | 0.8853 | — |
|  | X | 1.1475 | 0.26 |

2) Temperature profile:

| (1.67 M D-galactose, 0.01 M FeCl₂, pH 7.0, 120 min.) | | | |
|---|---|---|---|
| TEMPERATURE | SAMPLE | O.D. (540) | O.D. (X − B) |
| 20° C. | B | 0.5852 | — |
|  | X | 0.7433 | 0.1581 |
| 30° C. | B | 0.6127 | — |
|  | X | 0.8481 | 0.2354 |
| 40° C. | B | 0.6139 | — |
|  | X | 0.9124 | 0.2985 |
| 50° C. | B | 0.7033 | — |
|  | X | 1.0701 | 0.3664 |
| 55° C. | B | 0.6641 | — |
|  | X | 1.3474 | 0.6833 |
| 60° C. | B | 0.7805 | — |
|  | X | 1.6430 | 0.8625 |
| 65° C. | B | 0.6967 | — |
|  | X | 1.7798 | 1.0831 |
| 70° C. | B | 0.7321 | — |
|  | X | 0.8042 | 0.0721 |
| 80° C. | B | 0.8073 | — |
|  | X | 0.8063 | 0.00 |

3) Metallic ions:

| (1.67 M D-galactose, 0.005 M metallic ion, 60° C., 120 min.) | | | |
|---|---|---|---|
| METALLIC ION | SAMPLE | O.D. (540) | O.D. (X − B) | D-TAGATOSE (M) |
| None | B | 0.7210 | — | — |
|  | X | 1.5265 | 0.8055 | 0.037 |
| Manganese | B | 0.7972 | — | — |
|  | X | 1.7546 | 0.9574 | 0.044 |
| Magnesium | B | 0.8013 | — | — |
|  | X | 1.5903 | 0.7890 | 0.036 |
| Ferric | B | 0.8145 | — | — |
|  | X | 1.6148 | 0.8003 | 0.037 |
| Ferrous | B | 0.8583 | — | — |
|  | X | 1.6613 | 0.8030 | 0.037 |
| Cobalt | B | 0.8382 | — | — |
|  | X | 1.9146 | 1.0764 | 0.050 |
| Calcium | B | 0.8566 | — | — |
|  | X | 1.5673 | 0.7107 | 0.033 |
| Zinc | B | 0.8616 | — | — |
|  | X | 1.1160 | 0.2544 | 0.012 |

4) Manganese ion at different concentrations:

| (1.67 M D-galactose, Mn. different conc., 60° C., 120 min.) | | | |
|---|---|---|---|
| MANGANESE ION (M) | SAMPLE | O.D. (540) | O.D. (X − B) | D-TAGATOSE (M) |
| 0.000 | B | 0.6486 | — | — |
|  | X | 1.0934 | 0.4448 | 0.020 |
| 0.001 | B | 0.5429 | — | — |
|  | X | 1.4348 | 0.8919 | 0.041 |
| 0.003 | B | 0.7081 | — | — |
|  | X | 1.4681 | 0.7600 | 0.035 |
| 0.005 | B | 0.7232 | — | — |
|  | X | 1.6080 | 0.8848 | 0.040 |
| 0.007 | B | 0.7036 | — | — |
|  | X | 1.6093 | 0.9057 | 0.042 |
| 0.009 | B | 0.5967 | — | — |
|  | X | 1.7142 | 1.1175 | 0.051 |
| 0.011 | B | 0.7292 | — | — |
|  | X | 1.6625 | 0.9333 | 0.043 |
| 0.013 | B | 0.6976 | — | — |
|  | X | 1.7729 | 1.0753 | 0.049 |

When the bioconversion tests were conducted using a 10% w/w D-galactose substrate with various metallic ions while pH was maintained at 7.0 with a maleic acid buffer.

| SAMPLE[5] | METALLIC ION | TIME (HR) | % D-GALACTOSE | % D-TAGATOSE | % BIOCONV. |
|---|---|---|---|---|---|
| B | 0.01 Mn⁺⁺ | 0 | 9.1 | 0.0 | — |
| X | " | 6 | " | 1.1 | 12.1 |
| X | " | 24 | " | 2.5 | 27.5 |
| X | " | 48 | " | 3.0 | 33.0 |
| B | 0.005 Fe⁺⁺ | 0 | 9.4 | 0.0 | — |
| X | " | 6 | " | 1.0 | 10.6 |
| X | " | 24 | " | 2.9 | 30.9 |
| X | " | 48 | " | 2.2 | 23.4 |
| B | 0.005 Co⁺⁺ | 0 | 9.5 | 0.0 | — |
| X | " | 6 | " | 1.0 | 10.5 |
| X | " | 24 | " | 3.2 | 33.7 |
| X | " | 48 | " | 2.6 | 27.4 |
| B | Mn⁺⁺,Fe⁺⁺,Co⁺⁺ | 0 | 9.7 | 0.0 | — |
| X | " | 6 | " | 1.0 | 10.3 |
| X | " | 24 | " | 2.5 | 25.8 |
| X | " | 48 | " | 2.6 | 26.8 |

The maximum bioconversion was 33.7%

[5]Sample B comprised 1.0 ml. substrate and 2.0 ml. water and sample X comprised 1.0 ml. substrate and 2.0 ml. enzyme. Each mixture was incubated at 50° C.

[5]Sample B comprised 1.0 ml. substrate and 2.0 ml. water and sample X comprised 1.0 ml. substrate and 2.0 ml. enzyme. Each mixture was incubated at 50° C.

Example 10

Properties of L-arabinose Isomerase Produced from Different Micro-organisms

The enzyme L-arabinose isomerase was produced from three different bacteria genus according to the previous examples. These bacteria are:

1. *Lactobacillus pentosus* (ATCC 8041), non spore forming Gram positive rod-shaped cells, grow in short chains.
2. *Bacillus amyloliquefaciens* (IFO 3022), spore forming Grams positive rod-shaped cells, grow in long chains.
3. Arthrobacter sp. (ATCC 21920), non spore forming bacteria. A marked rod-coccus growth cycle occurs during growth in complex media. Both rods and coccoid forms are Gram positive but may be readily decolorized.

Properties of crude enzyme L-arabinose isomerase:

|  | L. pentosus | B. amylo. | Arthrobacter |
|---|---|---|---|
| Optimum pH | 5.5–7.0 | 7.0–7.5 | 6.5–7.0 |
| Optimum temp. | 70° C. | 65° C. | 65° C. |
| Km (D-galactose) | 1.10 M | 0.67 M | 0.87 M |
|  | (20%) | (12%) | (15%) |
| Optimum activator | ferrous | manganese | cobalt[6] |
| Activator conc. | 0.01 M | 0.001 M | 0.01 M (Mn.) |
| Bioconversion | 43% | 33% | 34% |

Enzyme properties were found to be slightly different depending on the microorganism source.
[6]Because cobalt ion is not acceptable by the FDA in food applications, the second best metallic ion (manganese) was evaluated for the optimum concentration.

[6]Because cobalt ion is not acceptable by the FDA in food applications, the second best metallic ion (manganese) was evaluated for the optimum concentration.

Example 11

Various D-galactose containing starting materials were evaluated for the production of D-tagatose using L-arabinose isomerase derived from the *Lactobacillus pentosus* of Example 1 and the procedures of Example 1 were followed. Bioconversion was conducted for 72 hours at 60° C. and pH was maintained at 6.5 using 0.1M malic acid. The HPLC results were as follows:

Example 12

Lactose concentrate powder was obtained by the condensation and spray drying of lactose permeate from the membrane processing of sweet cheese whey and/or milk. The chemical analysis of the powder was as follows:

| Moisture | 5% |
|---|---|
| Fat (db) | 0.5% |
| Ash (db) | 8.5% |
| Protein (db) | 5.0% |
| Lactose (db) | 83.5% |

Concentrated lactose permeate, 10,000 milliliters, having a concentration of 4.5% lactose and 19 grams of salt was passed through an MPT 10 nanofiltration membrane at a temperature of 50° C. and a pressure of 500 pounds per square inch. Three diafiltrations were carried out using 2,500 milliliters added deionized water for each diafiltration and a final diafiltration was carried out using 7,500 milliliters added deionized water. The filtered permeate, 4,000 milliliters, contained 9.0% lactose (80% recovery based on starting material) and 1.3 grams salt. 93.2% of the salt had been removed.

Lactose hydrolysis was carried out using Biolactase 30,000, a fungal enzyme derived from *Aspergillus oryzae*, sold by Quest International, Sarasota, Fla. Five hundred thousand units of enzyme total activity were immobilized on a glutaraldehyde-treated membrane for an FMC spiral unit. (One unit of enzyme activity is the amount of enzyme which will liberate one micromole of D-nitrophenol per minute at pH 4.5 and 37° C. under the conditions of the assay using O-nitrophenol beta-D-galacto pyranoside.) The 4 liters of salt-free concentrate was pumped through the FMC spiral unit at a flow rate of 25 milliliters per minute. The bioconversion conditions were 40° C. at a pH of 5.0. After 8 hours reaction time in a batch recirculation mode with a residence time of 20 minutes per cycle at a flow rate of 25 ml./minute, samples were taken and analyzed for % lactose, % galactose and % glucose using high performance liquid chromatography (HPLC). Samples of the starting material concentrate were also analyzed by HPLC. The results are illustrated in Table I.

| SAMPLE | % LACTOSE | % GLUCOSE | % D-GALACTOSE | % D-TAGATOSE | % BIO-CON.* |
|---|---|---|---|---|---|
| Hydrolyzed Lactose Std. | 0.7 | 16.8 | 10.4 | 4.8 | 31.5 |
| Hydrolyzed Liquid Whey | 0.25 | 12.2 | 7.8 | 4.3 | 35.5 |
| Hydrolyzed Whey Powder | 0.26 | 12.1 | 7.8 | 4.3 | 35.5 |
| Hydrolyzed Liq. Lactose Conc. | 0.33 | 14.8 | 9.8 | 4.0 | 29.0 |
| Hydrolyzed Lactose Powder | 0.6 | 15.8 | 9.7 | 3.7 | 27.6 |
| D-galactose Std. | 0.0 | 0.2 | 11.1 | 5.4 | 32.7 |
| D-galactose Std. | 0.0 | 0.4 | 11.3 | 4.8 | 29.8 |

$$*\% \text{ Bioconversion} = \frac{\% \text{ D-tagatose}}{(\% \text{ D-tagatose}) + (\% \text{ D-galactose})} \times 100$$

TABLE I

|  | % LACTOSE | % GALACTOSE | % GLUCOSE |
|---|---|---|---|
| Concentrate | 9.0 | 0.0 | 0.0 |
| Hydrolysate | 0.3 | 4.3 | 4.5 |

The hydrolyzed lactose (4 liters) was concentrated under vacuum at 65° C. to 1 liter. The concentrate had the following composition:

| | |
|---|---|
| % Lactose | 0.88 |
| % Galactose | 12.6 |
| % Glucose | 13.3 |

Alcohol fermentation was carried out in a 2 liter glass fermenter. 800 milliliters of hydrolyzed lactose plus one gram of ammonium phosphate was added and the glass fermenter was autoclaved for 45 minutes at 110° C. The fermenter was inoculated with a harvested cell mass of the yeast *Saccharomyces cerevisiae*, ATCC 287, which was grown in a 500 milliliter glucose medium on a shaker at 30° C. for 24 hours. The fermentation temperature was controlled at 30° C. using a jacketed fermenter cooled with water and the pH was maintained at 5.0 with 10% ammonium hydroxide. The fermentation was terminated as soon as glucose was reduced to less than 1% as determined by HPLC analysis. The results are illustrated in Table II.

TABLE II

| Age/Hours | % Lactose | % Galactose | % Glucose | % Ethanol |
|---|---|---|---|---|
| 0.0 | 0.88 | 13.3 | 12.6 | 0.0 |
| 16.0 | 0.89 | 12.4 | 7.5 | 2.5 |
| 24.0 | 0.91 | 12.7 | 1.2 | 6.0 |

The ethanol was separated from the fermentation broth by vacuum distillation at 40° C. 200 milliliters of distillate were recovered containing 6% ethanol. (Theoretical recovery would have been 12% ethanol, but difficulties were encountered with distillation condenser temperature which resulted in a loss of ethanol vapor.)

A 600 milliliter galactose fraction was concentrated by evaporation to 200 milliliters containing 45% galactose. Galactose in the concentrate was purified by passing the concentrate through a 60 cm×2.5 cm glass column packed with BIO-RAD AG 50W-X 8 cation exchange resin in the calcium form, available from Bio-Rad Laboratories, Richmond, Calif. Galactose was eluted from the column with deionized water.

The eluted galactose was concentrated under vacuum to a 70% solution. Crystallization of the 70% galactose solution was performed by adding 95% ethanol and cooling to below 0° C.

Recovery efficiency of galactose from the initial raw material was over 50%.

Example 13

Cells of the yeasts *Saccharomyces cerevisiae* ATCC 287 and ATCC 561 were separately propagated on a medium having the following composition:

| | % by Weight |
|---|---|
| Glucose | 20 |
| Galactose | 20 |
| Yeast extract | 0.3 |
| Malt extract | 0.3 |
| Peptone | 0.5 |

Phosphate was added as a buffer to maintain the pH at about 6.2.

Cells of the bacteria *Zymomonas mobilis* ATCC 10,988 and ATCC 31,822 were separately propagated on a medium having the following composition:

| | % by Weight |
|---|---|
| Glucose | 20 |
| Galactose | 20 |
| Yeast extract | 0.5 |

Phosphate was added as a buffer to maintain the pH at about 6.2.

Two samples of each yeast and bacteria culture were separately assayed by HPLC as the reactions proceeded to determine concentrations of glucose and galactose. The results are summarized in Table III.

TABLE III

| Sample | Culture | Age/Hour | % Glucose | % Galactose |
|---|---|---|---|---|
| 1 | ATCC 287 | 00.0 | 21.6 | 20.1 |
| | | 06.0 | 19.6 | 20.1 |
| | | 12.0 | 14.5 | 19.6 |
| | | 24.0 | 6.6 | 19.1 |
| | | 30.0 | 3.0 | 19.0 |
| | | 48.0 | 0.1 | 15.2 |
| 2 | ATCC 287 | 00.0 | 21.7 | 19.5 |
| | | 06.0 | 19.4 | 19.5 |
| | | 12.0 | 16.4 | 19.9 |
| | | 24.0 | 8.5 | 19.8 |
| | | 30.0 | 5.4 | 20.0 |
| | | 48.0 | 0.1 | 18.5 |
| 3 | ATCC 561 | 00.0 | 22.6 | 21.0 |
| | | 06.0 | 19.1 | 19.5 |
| | | 12.0 | 16.5 | 20.7 |
| | | 24.0 | 7.5 | 19.0 |
| | | 30.0 | 4.0 | 18.0 |
| | | 48.0 | 0.1 | 18.3 |
| 4 | ATCC 561 | 00.0 | 21.7 | 20.0 |
| | | 06.0 | 19.1 | 20.0 |
| | | 12.0 | 14.5 | 19.8 |
| | | 24.0 | 5.3 | 19.0 |
| | | 30.0 | 3.0 | 18.6 |
| | | 48.0 | 0.1 | 18.5 |
| 5 | ATCC 10988 | 00.0 | 19.5 | 20.2 |
| | | 06.0 | 18.6 | 20.1 |
| | | 12.0 | 16.3 | 19.9 |
| | | 24.0 | 8.3 | 19.3 |
| | | 30.0 | 2.9 | 19.1 |
| | | 48.0 | 0.1 | 18.5 |
| 6 | ATCC 10988 | 00.0 | 21.2 | 20.6 |
| | | 06.0 | 20.5 | 20.7 |
| | | 12.0 | 18.5 | 20.3 |
| | | 24.0 | 9.8 | 20.1 |
| | | 30.0 | 3.1 | 19.8 |
| | | 48.0 | 1.1 | 19.7 |
| 7 | ATCC 31822 | 00.0 | 19.7 | 18.6 |
| | | 06.0 | 18.4 | 18.8 |
| | | 12.0 | 16.2 | 18.4 |
| | | 24.0 | 8.7 | 18.1 |

TABLE III-continued

| Sample | Culture | Age/Hour | % Glucose | % Galactose |
|---|---|---|---|---|
|   |   | 30.0 | 2.3 | 17.6 |
|   |   | 48.0 | 0.1 | 17.1 |
| 8 | ATCC 31822 | 00.0 | 20.1 | 20.3 |
|   |   | 06.0 | 19.7 | 20.2 |
|   |   | 12.0 | 17.4 | 19.9 |
|   |   | 24.0 | 8.7 | 19.5 |
|   |   | 30.0 | 2.6 | 18.7 |
|   |   | 48.0 | 0.1 | 17.9 |

Table III illustrates the selectivity of both of the yeast and bacterial cultures in fermenting glucose over galactose.

Example 14

D-tagatose was purified by chromatographic separation from a mixture of D-tagatose and galactose by the following method:

Apparatus

Pump: Waters 590

Glass column: 2.5 cm i.d.×60 cm length, Kontes

Packing: Biorad cation exchange resin AG50W-X8 200–400 mesh

Detector: Waters 481 uv

Three-way stopcock 20 ml gastight syringe 50 ml graduate

Beakers or glass jars

Chemicals

Calcium oxide

Procedure

1. Biorad cation exchange resin was stirred with a saturated solution of calcium oxide until the supernatant liquid was alkaline, thereby putting it in the calcium form.

2. The glass column was packed with the resin and connected to the inlet to the Waters 590 pump and the outlet to the Waters 481 uv detector.

3. The sample mixture was injected through the three-way stopcock, with the pump off (up to 100 ml can be injected onto the column). The pump was started at 10 ml/min., and 50 ml fractions were collected from the detector outlet.

4. D-tagatose was separated from galactose after the 5th fraction (250–300 ml). Later fractions, containing an unknown late-eluting peak were recycled through the column, and the first six fractions (300 ml) were collected as pure D-tagatose.

5. All pure tagatose fractions were combined and concentrated by vacuum stripping.

6. Tagatose crystals were collected by addition of ethanol and cooling in a freezer.

Having set forth the general nature and some examples of the invention, the scope is now more particularly set forth in the appended claims.

What is claimed is:

1. A method of manufacturing D-tagatose from cheese whey, milk, or cheese whey and milk, comprising the following sequential steps:

subjecting the cheese whey, milk, or cheese whey and milk to ultrafiltration to make a lactose permeate;

hydrolyzing the lactose permeate to make a lactose hydrolysate comprised of D-galactose and glucose;

subjecting the lactose hydrolysate to fermentation conditions whereby the glucose is selectively fermented to ethanol;

separating the D-galactose from the ethanol, making a solution having a concentration of from about 10% to about 60% by weight D-galactose;

subjecting the solution of D-galactose to enzymatic isomerization with L-arabinose isomerase at an isomerization pH from about 5.5 to about 7.0 and a temperature from about 50° C. to about 70° C.; and wherein the yield of D-tagatose is from about 20% to about 45% by weight based on D-galactose.

2. The method of claim 1 comprising the further step of desalinating the lactose permeate before hydrolyzing.

3. The method of claim 2 wherein fermentation is caused by a yeast and/or bacteria.

4. The method of claim 3 wherein the yeast is Saccharomyces sp.

5. The method of claim 4 wherein the yeast is *Saccharomyces cerevisiae*.

6. The method of claim 3 wherein the bacteria is *Zymomonas mobilis*.

7. The method of claim 1 wherein metal ion activators are employed during isomerization.

8. The method of claim 7 wherein the metal ion activators are selected from the group consisting of manganese, magnesium, ferric, ferrous, cobalt, calcium and zinc.

* * * * *